United States Patent [19]

Laban

[11] 4,214,366
[45] Jul. 29, 1980

[54] DENTURE CONSTRUCTION

[76] Inventor: Ernst A. Laban, Burgemeester de Zeeuwstraat 36, Numansdorp, Netherlands

[21] Appl. No.: 951,649

[22] Filed: Oct. 16, 1978

[30] Foreign Application Priority Data

Oct. 20, 1977 [NL] Netherlands ............. 7711536
May 19, 1978 [NL] Netherlands ............. 7805476

[51] Int. Cl.³ .............................................. A61C 13/22
[52] U.S. Cl. ................................................. 433/189
[58] Field of Search ............... 32/DIG. 6, 10 A, 2

[56] References Cited

U.S. PATENT DOCUMENTS

| 3,729,825 | 5/1973 | Linkow et al. | 32/10 A |
| 3,748,739 | 7/1973 | Thibert | 32/10 A |
| 3,798,770 | 3/1974 | Mitchell | 32/DIG. 6 |

FOREIGN PATENT DOCUMENTS

| 1420594 | 10/1964 | France | 32/10 A |
| 2029344 | 1/1969 | France | 32/10 A |
| 2076270 | 1/1970 | France | 32/10 A |
| 2179157 | 6/1972 | France | 32/10 A |

*Primary Examiner*—Robert Peshock
*Attorney, Agent, or Firm*—Brumbaugh, Graves, Donohue & Raymond

[57] ABSTRACT

A denture construction comprising at least one implant and one or more elements to be positioned on or against the at least one implant and forming a denture or parts thereof or imitating same, which implant, or each of which implants, consists of a basic portion and one or more head portions, which head portions co-operate with the element, or the elements, in order to keep same in a proper relationship therewith after positioning of the implant or implants, in which construction the elements in the position of a point of contact with a head portion contain a magnet body, while each head portion and each element with magnet body are so formed that in the position where element and head portion contact each other a convex plane of the one contacts a flat plane of the other.

11 Claims, 7 Drawing Figures

U.S. Patent  Jul. 29, 1980  4,214,366
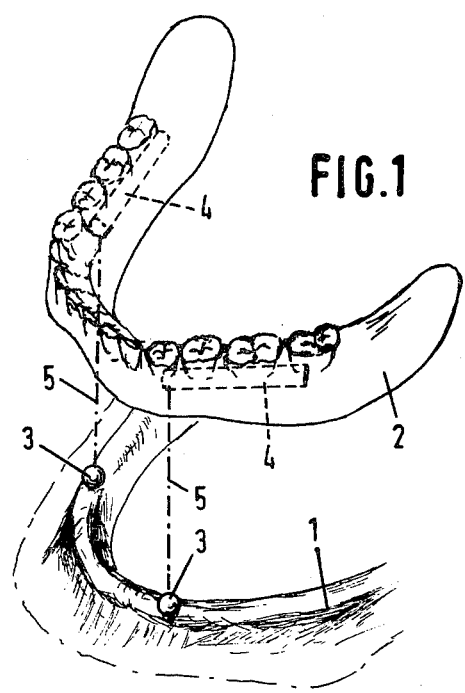
FIG.1
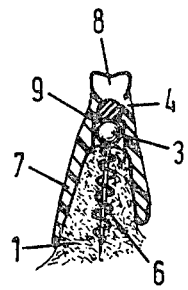
FIG.2
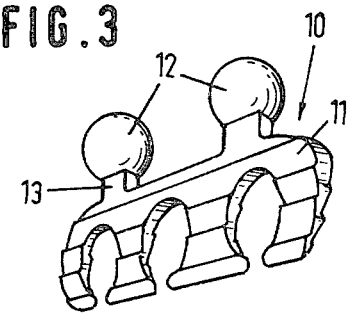
FIG.3
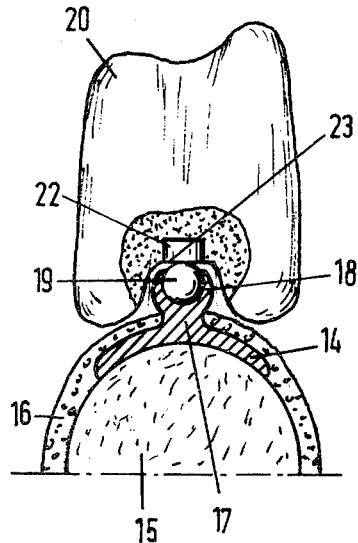
FIG.4
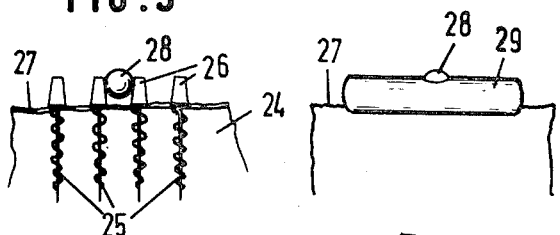
FIG.5
FIG.6
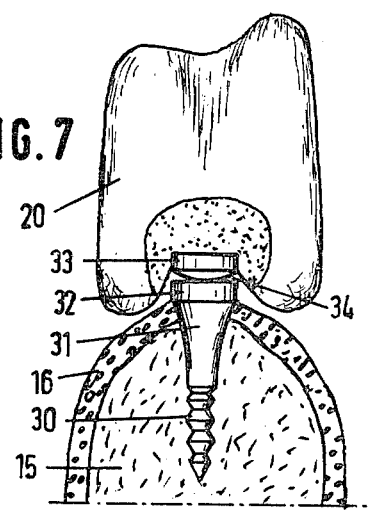
FIG.7

DENTURE CONSTRUCTION

The invention relates to a denture construction comprising at least one implant and one or more elements to be positioned on or against the at least one implant and forming a denture or parts thereof or imitating same, which implant, or each of which implants, consists of a basic portion and one or more head portions, which head portions co-operate with the element, or the elements, in order to keep same in a proper relationship therewith after positioning of the implant(s).

A like denture construction is known from U.S. Pat. No. 3,729,825. As appears from this publication, the blade-shaped basic portion of the implant, which blade-shaped portion should be inserted in a groove in the jaw-bone of a patient, may have a multiplicity of shapes. As a result of this, there is to be found the proper implant for any position in the jaw-bone and with any type of jaw-bone. In the known construction, the blade-shaped portion is provided with retention means consisting of raised edges extending into the longitudinal direction of the blade-shaped portion, which raised edges in cross-section have a toothed shape. Each implant is provided with at least one head portion, which in the known construction has the shape of a truncated pyramid. On the head portions are mounted the desired denture portions in such a manner that together with the implant(s) they constitute a rigid construction.

Since in the known construction the implant and the element mounted thereon constitute a rigid construction, this construction has the drawback that the forces exerted on the denture and the component elements thereof are transferred directly to the implant. This is in particular undesirable with respect to forces acting, or at least having a component of significance, in a plane perpendicular to the plane of the blade-shaped portion or the axis of the helical portion of the implant. In the end such laterally acting forces effect as it were a loosening of the implant. Moreover, the forces acting on the top end of a head portion may exert on the blade-shaped portion an influence which is analogous to a lever action. This phenomenon, too, may promote a loosening of the implant.

The object of the invention is to provide a denture construction in which the above-described drawback does not, or at least hardly, occur. This object is achieved by means of a denture construction in which the elements in the position of a point of contact with a head portion contain a magnet body, while each head portion and each element with magnet body are so formed that in the position where element and head portion contact each other a convex plane of the one contacts a flat plane of the other.

In a suitable embodiment of the construction according to the invention, each head portion of each implant contains an almost spherical portion, while the elements in the position of the point of contact with the spherical portion of a head portion contain a magnet body, which in the position of the point of contact has a flat plane. Each head portion of each implant may in a suitable manner consist of a sphere of magnetic material which may be coated with a thin layer of, for example, gold or teflon.

In an other embodiment, the head portion, or each head portion, of each implant consists of a sphere or ball of a magnetic material, contained in a ball bearing, which leaves free at least part of the sphere or ball at the top end of the head portion.

In the two said embodiments of the denture construction according to the invention the magnet body in the element, or in the elements, at a point of contact with a spherical portion of a head portion, furthermore in a suitable manner may have the shape of a bar magnet, which bar magnet is attached in the element in question in such a manner that part of the magnet near the end is adjacent to the head portion of the implant in question. Preferably, the portion of each bar magnet adjacent to the head portion is flat in the case that the end in question of the head portion of the implant itself is spherical. In the case that the head portion consists of a sphere or ball in a bearing, each magnet body in the element, or in the elements, at the point of contact with the sphere or ball, preferably has the shape of a flat cylindrical magnet which is attached in the element in question in such a manner that a head face of the magnet is adjacent to the sphere or ball.

In still an other embodiment of the construction according to the invention the, or each, head portion of a, or each, implant at its end is provided with a flat cylindrical magnet, while the element(s) in the position of the point of contact of element and head portion is/are provided with a magnet body having a convex face directed to the flat face of the cylindrical magnet of the head portion. This embodiment may also be so constructed that the magnet at the end of a head portion of an implant is provided with a convex face, while the corresponding magnet in the element shows a flat face directed to the convex face.

It will be clear that the invention is not limited to bar magnets or magnet discs. Other suitably formed magnet bodies are eligible as well.

In the denture construction according to the invention, lateral forces exerted on the elements forming the denture or parts thereof are not transferred to the implant or the implants, because the magnet against each head portion has a comparatively large extent of freedom of movement relative to the head portion in question. The magnet, and therefore, the denture element, not only can make a movement comparable to a hinge movement, but also a reciprocating movement is possible because the implant and the denture element do not constitute a rigid construction.

In order to arrive at a best suitable denture construction according to the invention, each part or denture element should be provided adjacent a head portion of an element co-operating therewith with a cavity having slightly larger dimensions than those of the head portion, so as to enable a movement relative to the head portion. Moreover, each magnet in the elements should have an optimum magnetic strength, so that each element, despite the freedom of movement, is kept against the head portions as strongly as possible. Small magnets of very great magnetic strength may, for example be made of samarium alloys. A samarium-cobalt alloy is a particularly suitable material.

For the basic portions of the implants of the denture construction according to the invention may be used the conventional titanium, but other materials may be employed as well. The spherical head portion(s) may, for example, consist of stainless steel, possibly coated with gold, teflon or an other suitable material. In the case of use of a head portion comprising a ball in a bearing, the ball may be of stainless steel and the bearing of gold. In the case of use of a head portion which itself at an end is provided with a magnet body, for this latter may be used a same type of magnet as was mentioned above for the elements.

The invention is not limited to implants having blade-shaped or helical basic portions to be attached in the jaw-bone. There may also be used implants of the subperiosteal type, of which the basic portion has a shape which is adapted to the shape of the jaw-bone, which basic portion is positioned on the jaw-bone but under the gums, having either a head portion with a ball in a bearing or a rigid spherical head portion, or a head portion having a magnet at the end.

For a further explanation of the technique of implants and denture constructions reference can be made to the book: Theories and Techniques of Oral Implantology, Vol. 1 (Saint Louis, 1970). Please note that on page 189 of said book there is question of magnetic implants. However, what are concerned there are implants which are magnetic, that is to say, small magnets which are "buried" in the jaw and exert an attraction force on magnets to be applied in the denture portions. As is set out in the relevant passage, this known technique has drawbacks. Inter alia, the buried magnets should lie close to the surface of the jaw, because otherwise a sufficient attraction force is not ensured. In that case, however, there is the danger of insufficient anchoring, the occurrence of pressure spots and "extraction" from the jaw owing to the permanent attraction force. In the construction according to the invention such drawbacks do not occur.

The invention will be explained with reference to the drawings, wherein:

FIG. 1 is a schematic view of a part of a jaw wherein are applied embodiments of implants according to the invention, as well as of an embodiment of a denture portion according to the invention to be mounted thereon;

FIG. 2 is a cross-sectional view of a jaw portion containing an embodiment of an implant according to the invention and having mounted thereon a denture portion;

FIG. 3 shows an embodiment of an implant according to the invention;

FIG. 4 is a cross-sectional view through a jaw portion containing still an other embodiment of an implant according to the invention and having mounted thereon an embodiment of a denture portion according to the invention;

FIGS. 5 and 6 show an other embodiment of the implant to be used according to the invention; and FIG. 7 shows in cross-section still an other embodiment of the denture construction according to the invention.

In FIG. 1 is shown schematically a part of a jaw 1, whereon has to be mounted a denture portion 2. In the case shown, jaw 1, which is, for example, the lower jaw of a patient, no longer contains teeth or molars, so that denture portion 2 is a complete lower set of artificial teeth. However, the invention is equally well applicable if jaw 1 still contains teeth and/or molars, so that there need be employed a denture portion 2 containing only a few teeth and/or molars. It will be clear that in these latter cases the implantation technique according to the invention is only employed if there is no possibility to attach the denture portions sufficiently firmly to the teeth and/or molars still present, without there being a risk that these latter become attacked or loosened as a result thereof.

In the case shown in FIG. 1 there is applied an implant in or on jaw 1. The head portions 3 of this implant extend above the jaw. In this embodiment of the implant according to the invention, these head portions themselves have the shape of a sphere. The basic portion of each implant which is embedded in the jaw may be helical or blade-shaped, while, if the basic portion is applied on the jaw but under the gums, it may be a plate having a shape adapted to the shape of the jaw in situ. The fact whether a blade-shaped or a helical basic portion of the implant is employed, or a plate-shaped basic portion of the (subperiosteal) implant, depends on the position where the implant is desired and on the condition of the jaw in question. All this is to be judged by the dentist who applies the implants.

In denture portion 2 are embedded two bar magnets 4. The bar magnets 4 are attached in denture 2 in such a manner that only that part which will co-operate with the spherical head portions 3 is exposed at the bottom side of the denture. When bar magnets 4 having a round cross-section are employed, to the faces of bar magnets 4 co-operating with the head portions 3 should be given preferably the flat shape to be used in a suitable embodiment of the invention. Instead of bar magnets 4 may also be employed small flat cylindrical magnets, as will be described hereafter with reference to FIG. 4. Dash-dotted lines 5 in FIG. 1 indicate how the portions adjacent the ends of magnets 4 will co-operate with the spherical head portions 3, when denture 2 is placed on jaw 1.

In FIG. 2 is given a cross-section of a part of a jaw having mounted thereon a denture portion, through an implant, all this according to an embodiment of the invention. As shown, a helical portion 6 of the implant is applied in jaw 1 and a spherical head portion 3 projects above the jaw. The denture portion comprises a body 7, the shape of which at the inner side is adapted to the shape of jaw 1. In body 7 are mounted in a conventional manner teeth and/or molars, one of which is indicated by 8. At the position of the spherical head portion 3 of the implant, body 7 contains a cavity 9 to accommodate the spherical head portion 3. In body 7 is attached a bar magnet 4 in such a manner that a part of the surface thereof is exposed adjacent the end in cavity 9. As a result of the magnetic effect of bar magnet 4, it is drawn against spherical head portion 3 and, consequently, the entire body 7 of the denture portion is retained on jaw 1. However, bar magnet 4, and therefore the entire denture portion, may move yet to some extent relative to spherical head portion 3, so that forces exerted laterally on the denture portion are not transferred to the implant, which does not happen with so far conventional implants having one or more rod-shaped head portions that were cemented in the denture portions used. Consequently, the in these known constructions possibly occurring phenomenon of loosening of the implant does not occur in the construction according to the invention.

In FIG. 3 is shown an embodiment of the implant according to the invention. The implant, which in general is indicated by 10, comprises a blade-shaped portion 11, on which are mounted two spherical head portions 12. The shape and the structure of the blade-shaped portion 11 are nothing special and, for example, correspond to the shape and structure of the blade-shaped portion of a known implant, as is defined in U.S. Pat. No. 3,729,825. Head portions 12 are mounted on projecting portions 13 on blade 11. The spherical portions 13 preferably consist of stainless steel, possibly coated with a thin layer of gold or teflon.

In FIG. 4 is shown in cross-section still an other embodiment of the denture construction according to the invention. In this embodiment, the implant is shown as a so-called subperiosteal implant, that is to say an implant, the basic portion 14 of which is plate-shaped. The shape of basic plate 14 is adapted to the shape of jaw-bone 15 in situ, while basic plate 14 is kept fixedly on jaw-bone 15 by gums 16. However, it is also possible to employ the embodiment as shown with an implant to be applied into the jaw, e.g. using a blade-shaped basic portion as shown in FIG. 3, or using a helical basic portion as shown in FIG. 2.

On basic portion 14 of the implant there is present the neck portion 17 which at its top end carries the head portion of the implant. This head portion consists of the ball bearing 18, wherein is mounted ball 19. Ball 19 is rotatable freely in bearing 18 in the manner as the ball of a ballpoint pen can rotate in its bearing. For example, ball 19 consists of a material which can be attracted by a magnet, such as stainless steel. Bearing 18 consists of a suitable material which is compatible with the objects for which the implant is used, e.g. of gold.

On the jaw and the implant applied thereon or therein there is positioned a denture portion. For example, a molar 20 constitutes part of this denture portion. At the bottom side in denture portion 20 there is provided a cavity 21 to accommodate the head portion of the implant. In denture portion 20 there is furthermore attached a flat cylindrical magnet 22 in such a manner that the flat surface 23 of the magnet disc is exposed at the side of the cavity 21. When denture portion 20 is positioned on the jaw and the implant, this surface 23 touches ball 19 and owing to the magnetic effect of magnet 22 this surface 23 is kept against ball 19. As a result of the fact that ball 19 can rotate freely in ball bearing 18, the entire denture portion 20 has some freedom of movement relative to the jaw and the implant, so that forces exerted on denture portion 20, e.g. during chewing, are not transferred in an undesirable manner to the implant.

The lateral forces on the implant are here even less than with a non-rotary ball. Here, too, there is present in the prosthesis a wide recess for the ball. Of course, also other magnet shapes and magnet dimensions can lead to the object in view—the sizes mentioned are not essential.

As magnet 22 in denture portion 20 may serve in a suitable manner a magnet of a samarium-cobalt alloy having a diameter of e.g. 2–4 mm and a height of e.g. 2–3 mm. Using a samarium-cobalt magnet, the magnet, even at such slight dimensions, has a force sufficient to ensure a proper retention of denture portion 20 on the jaw and implant.

In FIGS. 5 and 6 is shown an embodiment of an implant according to the invention and consisting of a multiple basic portion and a single head portion provided with a spherical portion. The implant as shown in these figures can be prepared in a suitable manner in situ. For example, this is done as follows. In jaw 24 there are arranged a plurality of separate implants having a helical basic portion 25 and a suitably shaped, e.g. trapezoidal, head portion 26 in such a manner that the head portions 26 project above the gums 27. Between two of the head portions 26 there is subsequently arranged a ball 28 of a suitable magnetic material, e.g. stainless steel, possibly coated with a thin layer of e.g. gold. The head portions 26 and ball 28 are then fixedly connected to each other by means of a beam 29 of e.g. gold (FIG. 6) to be applied around and over the head portions 26 and to be fixedly attached thereto, which beam is so shaped that the upper part of ball 28 projects above beam 29. Thus there is produced an implant consisting of a beam-shaped head portion with a spherical portion and a multiple basic portion formed by the screws 25. Of course, it is also possible to produce such an implant first as a whole and only then to apply same in the jaw. In that case, instead of screws, the multiple basic portion can then consist of pins provided with raised edges having a toothed shape, approximately analogous to the edges on the blade-shaped portions of the implant shown in FIG. 3.

On the implant shown in FIG. 6 can be positioned an element forming a denture portion, which element is provided with a magnet, preferably a flat portion of which is adjacent to the upper portion of ball 28. A magnet as shown in FIG. 4 (22) can serve very suitably for the purpose.

In FIG. 7 is shown in cross-section still an other embodiment of the denture construction according to the invention. This embodiment comprises an implant, the basic portion 30 of which is applied in the jaw 15. The basic portion 30 may be helical as in the embodiment shown in FIG. 2, or blade-shaped as in the embodiment according to FIG. 3. As is shown, the head portion 31 of the implant can be partly embedded in the jaw-bone 15 or can project there-above. To the upper end of head portion 31 there is attached a flat cylindrical magnet 32. Magnet 32 projects above the jaw-bone 15 and the surrounding gums 16. The denture portion or element 20, which is applied on the jaw 15, 16 and the implant 30, 31, 32, contains at the position of the point of contact with cylindrical magnet 32 on head portion 31 a cylindrical magnet 33, which at the side directed to magnet 32 shows a convex surface 34.

It will be clear that the construction according to FIG. 7 can also be designed reversely, that is to say, with a flat cylindrical magnet in the denture portion 20 and with an upwardly convex cylindrical magnet at the end of the head portion 31. What matters is only that at the position where a magnet is present a flat surface contacts a convex surface, so that forces exerted on the denture portion are transferred as little as possible, or not at all, to the implant(s).

I claim:

1. In a denture apparatus including an implant having a base portion for insertion in a patient's jaw and a head portion having a first surface for supporting a denture element, said apparatus further including a denture element having a second surface for directly engaging said first surface for mounting said denture element on said implant, the improvement wherein there are provided a magnetic element and a magnetically attractable element, one in each of said head portion and said denture element in the vicinity of said first and second surfaces, and wherein one of said surfaces is flat, and wherein the other of said surfaces is convex.

2. A denture apparatus according to claim 1, wherein said head portion of said implant has an almost spherical part and said second surface of said denture element is flat.

3. A denture apparatus according to claim 1 or 2 wherein said head portion of said implant comprises a ball of magnetic material coated with a thin layer of one of gold and teflon.

4. A denture apparatus according to claim 1 or 2, wherein said head portion of said implant comprises a sphere of magnetic material contained in a ball bearing which leaves a part of said sphere exposed at the top end of said head portion.

5. A denture apparatus according to claim 2, wherein said magnetic element is a bar magnet which is attached in said denture element with one end of said bar magnet being flat and adjacent to said head portion.

6. A denture apparatus according to claim 4, wherein said second surface of said denture element is a flat cylindrical magnet which is attached in said denture element in such a manner that an axial end face of the magnet is adjacent to said sphere.

7. A denture apparatus according to claim 1, wherein said head portion of said implant is a flat cylindrical magnet and said second surface of said denture element is convex.

8. A denture apparatus according to one of claims 1, 2, 6 or 7 wherein said base portion is adapted to be rigidly fixed to said patient's jaw and wherein said head portion is approximately spherical.

9. A denture apparatus according to claim 8 wherein said base comprises a plurality of closely-spaced independent elements having bottom helical-shaped portions which are adapted to be embedded in said jaw and said head portion comprises at least two trapezoidally-shaped head portions, corresponding to said helical-shaped bottom portions, and a ball of magnetic material between said head portions, said trapezoidally-shaped head portions fixedly connected to each other by a beam applied around and over said trapezoidally-shaped head portions, said beam shaped so that said magnetic ball projects above said beam.

10. A denture apparatus according to claim 7 comprising said base portion which is rigidly fixed to said patient's jaw and at least one head portion provided with a flat cylindrical magnet at the end of said head portion.

11. A denture apparatus according to one of claims 1, 2, 6 or 7, wherein said denture element comprises a part forming a denture member or portions thereof or imitating the same, provided with one or more magnetic elements.

* * * * *